United States Patent
Carranza Garzon et al.

(10) Patent No.: US 9,314,024 B2
(45) Date of Patent: Apr. 19, 2016

(54) HERBICIDAL COMPOSITIONS COMPRISING AMINOPYRALID AND BENTAZON

(71) Applicants: Nelson M. Carranza Garzon, Ibague (CO); Richard K. Mann, Franklin, IN (US)

(72) Inventors: Nelson M. Carranza Garzon, Ibague (CO); Richard K. Mann, Franklin, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/023,551

(22) Filed: Sep. 11, 2013

(65) Prior Publication Data

US 2014/0073507 A1 Mar. 13, 2014

Related U.S. Application Data

(60) Provisional application No. 61/700,672, filed on Sep. 13, 2012.

(51) Int. Cl.
*A01N 43/40* (2006.01)
*A01N 43/88* (2006.01)

(52) U.S. Cl.
CPC ............... *A01N 43/88* (2013.01); *A01N 43/40* (2013.01)

(58) Field of Classification Search
CPC ................................ A01N 43/40; A01N 43/88
USPC .................................................. 504/130, 132
See application file for complete search history.

(56) References Cited

U.S. PATENT DOCUMENTS

2006/0183637 A1* 8/2006 Loughner et al. ............. 504/101
2012/0015811 A1* 1/2012 Dave et al. ..................... 504/241

OTHER PUBLICATIONS

IP 88909D (Mar. 4, 2005).*
Milestone label, Dow AgroSciences, Aug. 29, 2005.*
HCAPLUS abstract 1976:26775 (1976).*

* cited by examiner

*Primary Examiner* — John Pak
(74) *Attorney, Agent, or Firm* — Michael R. Asam

(57) ABSTRACT

Provided herein are herbicidal compositions containing (a) aminopyralid or an agriculturally acceptable salt or ester thereof and (b) bentazon or an agriculturally acceptable salt thereof. The compositions provide synergistic weed control of undesirable vegetation, e.g., in rice, wheat, barley, oats, rye, sorghum, corn or maize, oilseed rape/canola, vegetables, pastures, grasslands, rangelands, fallowland, turf, tree and vine orchards, aquatics, industrial vegetation management or rights-of-way.

19 Claims, No Drawings

HERBICIDAL COMPOSITIONS COMPRISING AMINOPYRALID AND BENTAZON

CROSS REFERENCE TO RELATED APPLICATIONS

This application claims the benefit of U.S. Provisional Patent Application Ser. No. 61/700,672 filed Sep. 13, 2012, the disclosure of which is expressly incorporated herein by reference.

FIELD

Provided herein are herbicidal compositions comprising (a) 4-amino-3,6-dichloro-2-pyridinecarboxylic acid (aminopyralid) or an agriculturally acceptable ester or salt thereof and (b) 3-(1-methylethyl)-1H-2,1,3-benzothiadiazin-4(3H)-one 2,2-dioxide (bentazon) or an agriculturally acceptable salt thereof.

Provided herein are also methods of controlling undesirable vegetation comprising applying (a) aminopyralid or an agriculturally acceptable ester or salt thereof and (b) bentazon sodium salt.

BACKGROUND

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. However, there remains a need for compositions and methods that are effective in controlling undesirable vegetation.

SUMMARY

Provided herein are herbicidal compositions comprising a herbicidally effective amount of (a) aminopyralid, a compound of the formula (I)

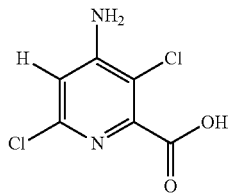 [SMILES: Nc1cc(Cl)nc(C(=O)O)c1Cl]
(I)

or an agriculturally acceptable salt or ester thereof, and (b) bentazon, a compound of the formula (II)

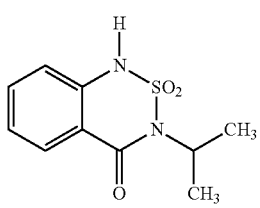 [SMILES: CC(C)N1C(=O)c2ccccc2NS1(=O)=O]
(II)

or an agriculturally acceptable salt thereof. The compositions may also contain an agriculturally acceptable adjuvant or carrier.

Provided herein are also methods of controlling undesirable vegetation comprising applying (a) aminopyralid, a compound of formula (I) or an agriculturally acceptable ester or salt thereof and (b) bentazon, a compound of formula (II) or an agriculturally acceptable salt thereof.

Exemplary salts of a compound of formula (I) include aminopyralid triisopropanolammonium salt and aminopyralid choline salt; exemplary salts of a compound of formula (II) include bentazon sodium salt.

DETAILED DESCRIPTION

Definitions

As used herein, the compound of formula (I) has the following structure:

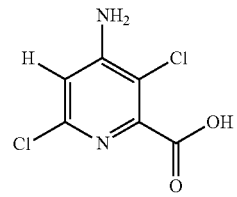
(I)

The compound of formula (I) can be identified by the CAS name 4-amino-3,6-dichloro-2-pyridinecarboxylic acid and by the common name aminopyralid. Exemplary uses of the compound of the formula (I) include controlling annual and perennial broad-leaved weeds in grasses, rangeland, pastures and other non-crop areas.

As used herein, the compound of formula (II) has the following structure:

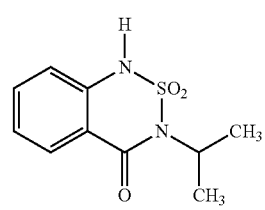
(II)

The compound of formula (II) can be identified by the CAS name 3-(1-methylethyl)-1H-2,1,3-benzothiadiazin-4(3H)-one 2,2-dioxide and by the common name bentazon, or bentazone. Bentazon is used as a contact herbicide for controlling *Anthemis, Chamomilla* and *Matricaria* spp., *Chrysanthemum segetum, Galium aparine, Lapsana communis* and *Stellaria media* and other broadleaf weeds in winter and spring cereals. Other crops include peanuts, corn/maize, peas, *Phaseolus* beans, rice and soybeans.

Exemplary salts include those derived from alkali or alkaline earth metals and those derived from ammonia and amines. Exemplary cations include sodium, potassium, magnesium, and aminium (ammonium) cations of the formula:

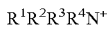

wherein $R^1$, $R^2$, $R^3$ and $R^4$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, triisopropanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, each of which is optionally substituted by one or more hydroxy, $C_1$-$C_4$ alkoxy or $C_1$-$C_4$ alkylthio groups, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

Compositions and Methods

Provided herein are herbicidal compositions comprising a herbicidally effective amount of (a) aminopyralid, a compound of the formula (I)

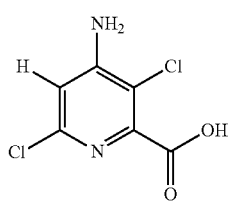 [SMILES: Nc1cc(Cl)nc(C(=O)O)c1Cl]

(I)

or an agriculturally acceptable salt or ester thereof, and (b) bentazon, a compound of the formula (II)

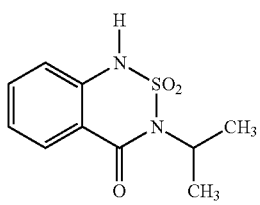

(II)

or an agriculturally acceptable salt thereof. Exemplary salts of a compound of formula (I) include the aminopyralid triisopropanolammonium salt; exemplary salts of a compound of formula (II) include the bentazon sodium salt.

Provided herein are also methods of controlling undesirable vegetation comprising contacting the vegetation or the locus thereof, i.e., area adjacent to the vegetation, with or applying to the soil or water to prevent the emergence or growth of vegetation a herbicidally effective amount (a) of the compound of formula (I) or agriculturally acceptable salt or ester thereof and (b) of the compound of formula (II) or agriculturally acceptable salt thereof. In certain embodiments, the methods employ the compositions described herein.

Furthermore, in some embodiments, the combination of compound (I) or agriculturally acceptable salt or ester thereof and compound (II), or an agriculturally acceptable salt thereof exhibits synergism, i.e., the herbicidal active ingredients are more effective in combination than when applied individually. Synergism has been defined as "an interaction of two or more factors such that the effect when combined is greater than the predicted effect based on the response of each factor applied separately." Senseman, S., Ed. Herbicide Handbook. 9$^{th}$ ed. Lawrence: Weed Science Society of America, 2007. In certain embodiments, the compositions exhibit synergy as determined by the Colby equation. (Colby, S. R. 1967. Calculation of the synergistic and antagonistic response of herbicide combinations. Weeds 1967 15, 20-22.)

In certain embodiments of the compositions and methods described herein, the compound of formula (I), i.e., the carboxylic acid, is employed. In certain embodiments, a carboxylate salt of the compound of formula (I) is employed. In certain embodiments of the compositions and methods described herein, the compound of formula (II), i.e., the 1H-benzo[c][1,2,6]thiadiazin-4(3H)-one 2,2-dioxide, is employed. In certain embodiments, the sodium salt of the compound of formula (II) is employed.

In some embodiments, the compound of formula (I) or salt or ester thereof and the compound of formula (II) or salt, thereof, are formulated in one composition, tank mixed, applied simultaneously, or applied sequentially.

Herbicidal activity is exhibited by the compounds when they are applied directly to the plant or to the locus of the plant at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. In some embodiments, the compositions described herein are applied as a post-emergence application, pre-emergence application, or in-water application to flooded paddy rice or water bodies (e.g., ponds, lakes and streams), to relatively immature undesirable vegetation to achieve the maximum control of weeds.

In some embodiments, the compositions and methods provided herein are utilized to control weeds in crops or other settings, including but not limited to direct-seeded, water-seeded and transplanted rice, wheat, barley, oats, rye, sorghum, corn/maize, pastures, grasslands, rangelands, fallowland, turf, tree and vine orchards, aquatics, industrial vegetation management (IVM) and rights-of-way.

In certain embodiments, the compositions and methods provided herein are utilized to control weeds in rice. In certain embodiments, the rice is direct-seeded, water-seeded, or transplanted rice.

The compositions and methods described herein are used to control undesirable vegetation in glyphosate tolerant-, glufosinate tolerant-, dicamba tolerant-, phenoxy auxin tolerant-, pyridyloxy auxin tolerant-, aryloxyphenoxypropionate tolerant-, acetyl CoA carboxylase (ACCase) inhibitor tolerant-, imidazolinone tolerant-, acetolactate synthase (ALS) inhibitor tolerant-, 4-hydroxyphenyl-pyruvate dioxygenase (HPPD) inhibitor tolerant-, protoporphyrinogen oxidase (PPO) inhibitor tolerant-, triazine tolerant- and bromoxynil tolerant-crops (such as, but not limited to, soybean, cotton, canola/oilseed rape, rice, cereals, corn/maize, turf, etc), for example, in conjunction with glyphosate, glufosinate, dicamba, phenoxy auxins, pyridyloxy auxins, aryloxyphenoxypropionates, ACCase inhibitors, imidazolinones, ALS inhibitors, HPPD inhibitors, PPO inhibitors, triazines, and bromoxynil. The compositions and methods may be used in controlling undesirable vegetation in crops possessing multiple or stacked traits conferring tolerance to multiple chemistries and/or inhibitors of multiple modes of action. In some embodiments, the compound of formula (I) or salt or ester thereof and the compound of formula (II) or salt thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation or as a tank mix.

The compositions and methods provided herein are utilized to control undesirable vegetation. Undesirable vegetation includes, but is not limited to, undesirable vegetation that occurs in rice, cereals, range and pasture, row crops (e.g., corn/maize, soybean, cotton, canola/oilseed rape), turf, trees, vines, ornamental species and non-crop settings, (e.g., rights-of-way, IVM).

In some embodiments, the methods provided herein are utilized to control undesirable vegetation in rice. In certain embodiments, the undesirable vegetation is *Cyperus difformis* L. (smallflower flatsedge, CYPDI), *Cyperus esculentus* L. (yellow nutsedge, CYPES), *Cyperus iria* L. (rice flatsedge, CYPIR), *Cyperus rotundus* L. (purple nutsedge, CYPRO), *Eleocharis* species (ELOSS), *Fimbristylis miliacea* (L.) Vahl (globe fringerush, FIMMI), *Schoenoplectus juncoides* Roxb. (Japanese bulrush, SPCJU), *Schoenoplectus maritimus* L. (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea hederacea* (L.) Jacq. (ivyleaf morningglory, IPOHE), *Lindernia dubia* (L.) Pennell (low false pimpernel, LIDDU), *Monochoria korsakowii* Regel & Maack (monochoria, MOOKA), *Monochoria vaginalis* (Burm. F.) C. Presl ex Kuhth, (monochoria, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp sesbania, SEBEX), or *Sphenoclea zeylanica* Gaertn. (gooseweed, SPDZE).

In some embodiments, the methods provided herein are utilized to control undesirable vegetation in cereals. In certain embodiments, the undesirable vegetation is *Cirsium arvense* (L.) Scop. (Canada thistle, CIRAR), *Galium aparine* L. (catchweed bedstraw, GALAP), *Kochia scoparia* (L.) Schrad. (kochia, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the methods provided herein are utilized to control undesirable vegetation in range and pasture. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly sida, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G.H. Weber ex Wiggers (dandelion, TAROF), *Trifolium repens* L. (white clover, TRFRE), or *Urtica dioica* L. (common nettle, URTDI).

In some embodiments, the methods provided herein are utilized to control undesirable vegetation found in row crops. In certain embodiments, the undesirable vegetation is *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Asclepias syriaca* L. (common milkweed, ASCSY), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Erigeron bonariensis* L. (hairy fleabane, ERIBO), *Erigeron canadensis* L. (Canadian fleabane, ERICA), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Sida spinosa* L. (prickly sida, SIDSP), *Sinapis arvensis* L. (wild mustard, SINAR), *Solanum ptychanthum* Dunal (eastern black nightshade, SOLPT), or *Xanthium strumarium* L. (common cocklebur, XANST).

In some embodiments, the compositions and methods provided herein are utilized to control undesirable vegetation consisting of grass, broadleaf and sedge weeds. In certain embodiments, the compositions and methods provided herein are utilized to control undesirable vegetation including *Corchorus*, *Cyperus* and *Phyllanthus*.

In some embodiments, the combination of compound (I) or agriculturally acceptable ester or salt thereof and the compound of formula (II) or agriculturally acceptable salt thereof are used to control *Cyperus iria* L. (rice flatsedge, CYPIR), *Phyllanthus niruri* L. (gripeweed, PYLNI) and *Corchorus* spp (jute, CRGSS).

The compound of formula (I) or agriculturally acceptable salt or ester thereof and the compound of formula (II) or agriculturally acceptable salt thereof may be used to control herbicide resistant or tolerant weeds. The methods employing the combination of a compound of formula (I) or agriculturally acceptable salt or ester thereof and the compound of formula (II) or agriculturally acceptable salt thereof and the compositions described herein may also be employed to control herbicide resistant or tolerant weeds. Exemplary resistant or tolerant weeds include, but are not limited to, biotypes resistant or tolerant to acetolactate synthase (ALS) inhibitors, photosystem II inhibitors, acetyl CoA carboxylase (ACCase) inhibitors, synthetic auxins, photosystem I inhibitors, 5-enolpyruvylshikimate-3-phosphate (EPSP) synthase inhibitors, microtubule assembly inhibitors, lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, multiple chemical classes, and multiple herbicide modes-of-action.

In certain embodiments of the compositions and methods described herein, the compound of formula (I) or salt or ester thereof is used in combination with the compound of formula (II) or salt thereof. With regard to the compositions, in some embodiments, the ratio of the acid equivalent weight of the compound of formula (I) or salt or ester thereof to the weight of the compound of formula (II) or agriculturally acceptable salt thereof is within the range from about 1:720 to about 1:1. In certain embodiments, the ratio of the compound of the acid equivalent weight of the compound of formula (I) or salt or ester thereof to the weight of the compound of formula (II) or agriculturally acceptable salt thereof is within the range from about 1:135 to about 1:4. In certain embodiments, the ratio of the compound of the acid equivalent weight of the compound of formula (I) or salt or ester thereof to the weight of the compound of formula (II) or agriculturally acceptable salt thereof is within the range from about 1:90 to about 1:6. In certain embodiments, the ratio of the compound of the acid equivalent weight of the compound of formula (I) or salt or ester thereof to the weight of the compound of formula (II) or agriculturally acceptable salt thereof is within the range from about 1:45 to about 1:12. In certain embodiments, the compositions provided herein comprise the compound of formula (I) or its triisopropanolammonium salt and the compound of formula (II) or its sodium salt. In one embodiment, the composition comprises the compound of formula (I) or its triisopropanolammonium salt in combination with the compound of formula (II) or its sodium salt. In one embodiment, the composition comprises the triisopropanolammonium salt of the compound of formula (I) and the compound of formula (II), wherein the weight ratio of the triisopropanolammonium salt of the compound of formula (I) and the compound of formula (II) is from about 1:100 to about 1:1, from about 1:75 to about 1:5, from about 1:66 to about 1:7, from about 1:60 to about 1:8, from about 1:55 to about 1:10 or from about 1:45 to about 1:12. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate from about 108 grams active ingredient per hectare (g ai/ha) to about 2360 g ai/ha based on the total amount of active ingredients in the composition. In certain embodiments, the composition is applied at an application rate from about 184 g ai/ha to about 196 g ai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and a compound of formula (II) or agriculturally acceptable salt thereof, e.g., sequentially or simultaneously. In some embodiments, the compound of formula (II) or agriculturally acceptable salt thereof is applied at a rate from about 100 g ai/ha to about 2500 g ai/ha and the compound of formula (I) or salt or ester thereof is applied at a rate from about 2 grams acid equivalent per hectare (g ae/ha) to about 100 g ae/ha. In some embodiments, the compound of formula (II) or agriculturally acceptable salt thereof is applied at a rate from about 105 g ai/ha to about 2240 g ai/ha and the compound of formula (I) or salt or ester thereof is applied at a rate from about 4 grams acid equivalent per hectare (g ae/ha) to about 16 g ae/ha. In some embodiments, the compound of formula (II) or agriculturally acceptable salt thereof is applied at a rate of about 125 to about 1500 g ai/ha and the compound of formula (I) or salt or ester thereof is applied at a rate from about 4 g ae/ha to about 60 g ae/ha. In some embodiments, the compound of formula (II) or agriculturally acceptable salt thereof is applied at a rate of about 170 to 200 g ai/ha and the compound of formula (I) or salt or ester thereof is applied at a rate from about 4 g ae/ha to about 16 g ae/ha. In certain embodiments, the methods utilize the compound of formula (I), or its triisopropanolammonium salt and the compound of formula (II) or its sodium salt. In certain embodiments, the methods and compositions utilizing a compound of formula (I) or salt or ester thereof in combination with a compound of formula (II) or its sodium salt are used to control CYPIR, CRGSS or PYLNI.

The components of the mixtures described herein can be applied either separately, sequentially, tankmixed or as part of a multipart herbicidal system.

The mixtures described herein can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the compositions and methods described herein include, but are not limited to: 4-CPA, 4-CPB, 4-CPP, 2,4-D, 2,4-D choline salt, 2,4-D esters and amines, 2,4-DB, 3,4-DA, 3,4-DB, 2,4-DEB, 2,4-DEP, 3,4-DP, 2,3,6-TBA, 2,4,5-T, 2,4,5-TB, acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, benzadox, benzfendizone, benzipram, benzobicyclon, benzofenap, benzofluor, benzoylprop, benzthiazuron, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorprocarb, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam, cloransulam-methyl, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop-methyl, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethbenzamide, ethidimuron, ethiolate, ethobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenquinotrione, fenteracol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, flurtamone, fluthiacet, fomesafen, foramsulfuron, fosamine, fumiclorac, furyloxyfen, glufosinate, glufosinate-ammonium, glufosinate-P-ammonium, glyphosate, halosafen, halosulfuron-methyl, haloxydine, haloxyfop-methyl, haloxyfop-P-methyl, hexachloroacetone, hexaflurate, hexazinone, imazamethabenz, imazamox, imazapic, imazapyr, imazaquin, imazosulfuron, indanofan, indaziflam, iodobonil, iodomethane, iodosulfuron, iodosulfuron-ethyl-sodium, iofensulfuron, ioxynil, ipazine, ipfencarbazone, iprymidam, IR-5790, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, metsulfuron-methyl, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, orthodichlorobenzene, orthosulfamuron, oryzalin, oxadiargyl, oxadiazon, oxapyrazon, oxasulfuron, oxaziclomefone, oxyfluorfen, paraflufen-ethyl, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen-ethyl, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-sodium, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluoron, thaxtomin A, thaxtomin B, thenylchlor, thiazafluoron, thiazopyr, thidiazimin, thidiazuron, thiencarbazone-methyl, thifensulfuron, thifensulfuron-methyl, thiobencarb, tiocarbazil, tioclorim, topramezone, tralkoxydim, triafamone, tri-allate, triasulfuron, triaziflam, tribenuron, tribenuron-methyl, tricamba, triclopyr choline salt, triclopyr esters and salts, tridiphane, trietazine, trifloxysulfuron, trifluralin, triflusulfuron, trifop, trifopsime, trihydroxytriazine, trimeturon, tripropindan, tritac tritosulfuron, vernolate, xylachlor and salts, esters, optically active isomers and mixtures thereof.

In some embodiments, the compositions described herein are employed in combination with one or more herbicide safeners, such as 1-MCP, AD-67 (MON 4660), benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, jiecaowan, jiecaoxi, mefenpyr-diethyl, mephenate, naphthalic anhydride (NA), oxabetrinil, R29148 and N-phenyl-sulfonylbenzoic acid amides, to enhance their selectivity. In some embodiments, the safeners are employed in rice, cereal, corn, or maize settings. In some embodiments, the safener is cloquintocet or an ester or salt thereof. In certain embodiments, cloquintocet is utilized to antagonize harmful effects of the compositions on rice and cereals. In some embodiments, the safener is cloquintocet (mexyl).

In some embodiments, compositions provided herein further comprise at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank mixed.

Suitable agricultural adjuvants and carriers include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG (400) dioleate-99.

Liquid carriers that can be employed include water and organic solvents. The organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. In certain embodiments, water is the carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

In some embodiments, the compositions described herein further comprise one or more surface-active agents. In some embodiments, such surface-active agents are employed in both solid and liquid compositions, and in certain embodiments those designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkyl-naphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, and in certain embodiments, methyl esters.

In some embodiments, these materials, such as vegetable or seed oils and their esters, can be used interchangeably as an agricultural adjuvant, as a liquid carrier or as a surface active agent.

Other exemplary additives for use in the compositions provided herein include but are not limited to compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

In some embodiments, the concentration of the active ingredients in the compositions described herein is from about 0.0005 to 98 percent by weight. In some embodiments, the concentration is from about 0.0006 to 90 percent by weight. In compositions designed to be employed as concentrates, the active ingredients, in certain embodiments, are present in a concentration from about 0.1 to 98 weight percent, and in certain embodiments about 0.5 to 90 weight percent. Such compositions are, in certain embodiments, diluted with an inert carrier, such as water, before application. The diluted compositions usually applied to weeds or the locus of weeds contain, in certain embodiments, about 0.0003 to 10.5 weight percent active ingredient and in certain embodiments contain about 0.0008 to 10.0 weight percent.

The present compositions can be applied to weeds or their locus by the use of conventional ground or aerial dusters, sprayers, and granule applicators, by addition to irrigation or paddy water, and by other conventional means known to those skilled in the art.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

Evaluation of Postemergence Herbicidal Activity of Mixtures Under Field Conditions Methodology These trials were conducted under field conditions in Espinal, Colombia. Trial sites were located in commercially grown fields of common rice (*Oryza sativa*). The rice crop was grown using normal cultural practices for fertilization, seeding, and maintenance to ensure good growth of the crop and the weeds. The trials were conducted using normal research methodology. Trial plots were 2 meters (m) wide by 5 m long. All treatments were applied using a randomized complete block trial design with 4 replications per treatment. The trial sites had naturally occurring populations of weeds. The weed spectrum included, but was not limited to, *Cyperus iria* L. (rice flatsedge, CYPIR), *Phyllanthus niruri* L. (gripeweed, PYLNI) and *Corchorus* spp (jute, CRGSS). The plots were treated with a postemergence foliar application 19 days after emergence of the rice.

Treatments consisted of tank mixes of aminopyralid triisopropanolammonium salt (MILESTONE 240SL) and commercially available formulations of bentazon herbicide (BASAGRAN 480SL). The application volume was 200 liters per hectare (L/ha) of water. All application were made using precision gas hand sprayers with a 2 m boom using flat fan (8002) nozzles to broadcast the treatments over the top of the rice and weeds.

Evaluation

The treated plots and control plots were rated blind at various intervals after application. Ratings were based on Percent (%) Visual weed control, where 0 corresponds to no injury and 100 corresponds to complete kill.

Data were collected for all trials and analyzed using various statistical methods.

Colby's equation was used to determine the herbicidal effects expected from the mixtures (Colby, S. R. Calculation of the synergistic and antagonistic response of herbicide combinations. *Weeds* 1967 15, 20-22).

The following equation was used to calculate the expected activity of mixtures containing two active ingredients, A and B:

Expected=$A+B-(A\times B/100)$

A=observed efficacy of active ingredient A at the same concentration as used in the mixture;

B=observed efficacy of active ingredient B at the same concentration as used in the mixture.

The results are summarized in Table 1.

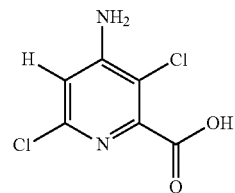

or an agriculturally acceptable salt or ester of thereof, and
  (b) bentazon, a compound of the formula (II)

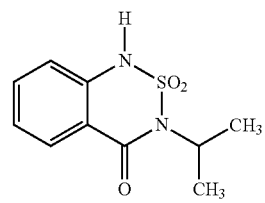 [SMILES: CC(C)N1C(=O)c2ccccc2NS1(=O)=O]

or an agriculturally acceptable salt of thereof, wherein the ratio of the acid equivalent weight of the compound of formula (I) or agriculturally acceptable salt or ester thereof to the weight of the compound of formula II or agriculturally acceptable salt thereof is from about 1:55 to about 1:10.

2. The composition of claim 1, wherein (a) is the triisopropanolammonium salt or choline salt of compound (I).

3. The composition of claim 1, wherein (a) is the compound of formula (I), which is the carboxylic acid.

4. The composition of claim 1, wherein the (b) is the sodium salt of compound (II).

5. The composition of claim 1, wherein the ratio is from about 1:45 to about 1:12.

6. The composition of claim 1, further comprising an agriculturally acceptable adjuvant or carrier.

TABLE 1

Synergistic Herbicidal Activity 29 days after application in a Field Trial in Espinal, Colombia.

| Aminopyralid | Bentazon | Visual Weed Control (%)—29 DAA | | | | | |
|---|---|---|---|---|---|---|---|
| | | CYPIR | | CRGSS | | PYLNI | |
| g ae/ha | g ai/ha | Obs | Exp | Obs | Exp | Obs | Exp |
| 4 | — | 0 | — | 48 | — | 0 | — |
| 8 | — | 0 | — | 70 | — | 0 | — |
| 16 | — | 41 | — | — | — | 0 | — |
| — | 180 | 74 | — | 80 | — | 19 | — |
| 4 | 180 | 94 | 74 | 98 | 90 | 93 | 19 |
| 8 | 180 | 93 | 74 | 100 | 94 | 89 | 19 |
| 16 | 180 | 95 | 85 | — | — | 93 | 19 |

CYPIR—rice flatsedge (*Cyperus iria*)
CRGSS—jute (*Corchorus* sp)
PYLNI—gripeweed (*Phyllanthus niruri* L)
g ae/ha—grams of acid equivalent per hectare
g ai/ha—grams of active ingredient per hectare
Obs—Observed percent weed control
Exp—Expected percent weed control as predicted by Colby equation
DAA = days after application

What is claimed is:

1. A herbicidal composition comprising a synergistic herbicidally effective amount of: (a) aminopyralid, a compound of the formula (I)

7. A method of controlling undesirable vegetation which comprises contacting the vegetation or the locus thereof with or applying to soil or water the composition of claim 1.

8. A method of controlling undesirable vegetation which comprises contacting the vegetation or the locus thereof with or applying to the soil or water a herbicidally effective amount of: (a) aminopyralid, a compound of the formula (I)

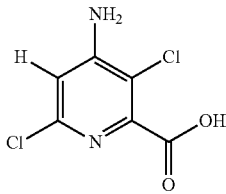

or an agriculturally acceptable salt or ester thereof, and (b) bentazon, a compound of the formula (II)

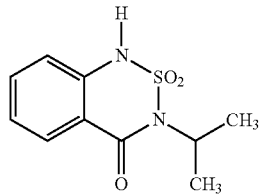

or an agriculturally acceptable salt thereof, wherein the ratio of the acid equivalent weight of the compound of formula (I) or agriculturally acceptable salt or ester thereof to the weight of the compound of formula II or agriculturally acceptable salt thereof is from about 1:55 to about 1:10.

9. The method of claim 8, wherein the undesirable vegetation is controlled in rice, wheat, barley, oats, rye, sorghum, corn, maize, pastures, grasslands, rangelands, fallowland, turf, tree and vine orchards, industrial vegetation management or rights-of-way.

10. The method of claim 8, wherein the undesirable vegetation is mature or immature.

11. The method of claim 10, wherein the (a) and (b) are applied to water.

12. The method of claim 11, wherein the water is part of a flooded rice paddy.

13. The method of claim 8, wherein the (a) and (b) are applied pre-emergence.

14. The method of claim 8, wherein the (a) and (b) are applied post-emergence.

15. The method of claim 8, wherein the undesirable vegetation is controlled in glyphosate-, glufosinate-, dicamba-, phenoxy auxins-, pyridyloxy auxins-, aryloxyphenoxypropionates-, acetyl CoA carboxylase inhibitors-, imidazolinones-, acetolactate synthase inhibitors-, 4-hydroxyphenyl-pyruvate dioxygenase inhibitors-, protoporphyrinogen oxidase inhibitors-, triazines-, or bromoxynil-tolerant crop.

16. The method of claim 15, wherein the tolerant crop possesses multiple or stacked traits conferring tolerance to multiple herbicides or inhibitors of multiple modes of action.

17. The method of claim 8, wherein the undesirable vegetation comprises a herbicide resistant or tolerant weed.

18. The method of claim 17, wherein the resistant or tolerant weed is a biotype with resistance or tolerance to multiple herbicides, multiple chemical classes, or inhibitors of multiple herbicide modes-of-action.

19. The method of claim 17, wherein the resistant or tolerant weed is a biotype resistant or tolerant to acetolactate synthase inhibitors, photosystem II inhibitors, acetyl CoA carboxylase inhibitors, synthetic auxins, photosystem I inhibitors, 5-enolpyruvylshikimate-3-phosphate synthase inhibitors, microtubule assembly inhibitors, lipid synthesis inhibitors, protoporphyrinogen oxidase inhibitors, carotenoid biosynthesis inhibitors, very long chain fatty acid inhibitors, phytoene desaturase inhibitors, glutamine synthetase inhibitors, 4-hydroxyphenyl-pyruvate-dioxygenase inhibitors, mitosis inhibitors, cellulose biosynthesis inhibitors, herbicides with multiple modes-of-action, quinclorac, arylaminopropionic acids, difenzoquat, endothall, or organoarsenicals.

* * * * *